(12) United States Patent
Liu

(10) Patent No.: US 11,865,106 B2
(45) Date of Patent: Jan. 9, 2024

(54) METHODS AND COMPOSITIONS FOR TREATMENT OF INFLAMMATORY BOWEL DISEASE

(71) Applicant: SHENZHEN HIGHTIDE BIOPHARMACEUTICAL, LTD., Shenzhen (CN)

(72) Inventor: Liping Liu, Manassas, VA (US)

(73) Assignee: SHENZHEN HIGHTIDE BIOPHARMACEUTICAL, LTD., Shenzhen (CN)

( * ) Notice: Subject to any disclaimer, the term of this patent is extended or adjusted under 35 U.S.C. 154(b) by 0 days.

(21) Appl. No.: 16/632,489

(22) PCT Filed: Aug. 8, 2018

(86) PCT No.: PCT/CN2018/099425
§ 371 (c)(1),
(2) Date: Jan. 20, 2020

(87) PCT Pub. No.: WO2019/029578
PCT Pub. Date: Feb. 14, 2019

(65) Prior Publication Data
US 2020/0237734 A1    Jul. 30, 2020

Related U.S. Application Data

(60) Provisional application No. 62/544,722, filed on Aug. 11, 2017.

(51) Int. Cl.
| | |
|---|---|
| *A61K 31/4375* | (2006.01) |
| *A61P 1/00* | (2006.01) |
| *A61K 31/202* | (2006.01) |
| *A61K 31/593* | (2006.01) |
| *A61K 35/60* | (2006.01) |
| *A61K 45/06* | (2006.01) |

(52) U.S. Cl.
CPC ........ *A61K 31/4375* (2013.01); *A61K 31/202* (2013.01); *A61K 31/593* (2013.01); *A61K 35/60* (2013.01); *A61K 45/06* (2013.01); *A61P 1/00* (2018.01)

(58) Field of Classification Search
CPC .. A61K 31/4375; A61K 31/202; A61K 35/60; A61P 1/00
See application file for complete search history.

(56) References Cited

U.S. PATENT DOCUMENTS 11,369,573 B2 *   6/2022   Liu ................ A61K 31/4745
2021/0300915 A1 *  9/2021   Liu ..................... A61P 3/06

FOREIGN PATENT DOCUMENTS

WO    WO-2015034984 A1 *   3/2015 ............. A61K 33/42

OTHER PUBLICATIONS

Covington (Omega-3 Fatty Acids, American Family Physician, Jul. 1, 2004, vol. 70, No. 1). (Year: 2004).*
Yan (Berbeine promotes recovery of colitis and inhibits inflammatory responses in colonic macrophages and epithelial cells in DSS-treated mice, Am J Physiol Gast Liver Physiol, 302: G504-G514, 2012) (Year: 2012).*
Harris (Fish Oil supplementation: Evidence for health benefits, Cleveland Clinic Journal of Medicine, vol. 71, No. 3, Mar. 2004) (Year: 2004).*
Yan (Berberine promotes recovery of colitis and inhibits inflammatory responses in colonic macrophages and epithelial cells in DSS-treated mice, Am J Physiol Gastrointest Liver Physiol, Mar. 1, 2012; 302(5): G504-G514) (Year: 2012).*
https://themedicinemaker.com/discovery-development/beyond-keeping-up-appearances) Apr. 26, 2016 (Year: 2016).*

* cited by examiner

*Primary Examiner* — Terry A McKelvey
*Assistant Examiner* — Jacob A Boeckelman
(74) *Attorney, Agent, or Firm* — Milstein Zhang & Wu LLC

(57) ABSTRACT

The invention provides novel pharmaceutical compositions of berberine or a derivative or analog of berberine, or a salt thereof, in combination with one or more omega-3 fatty acids or esters thereof, and methods of their use in treating inflammatory bowel disease.

5 Claims, 7 Drawing Sheets

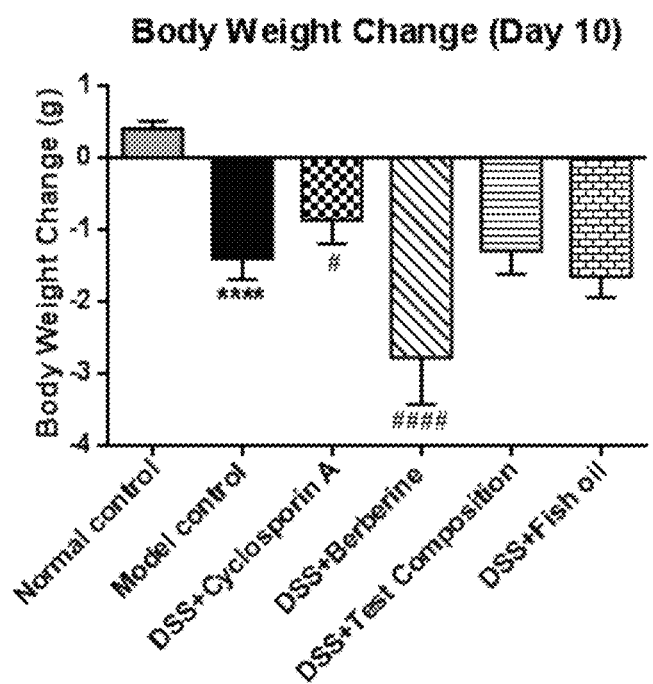
\*\*\*\* *P*<0.0001 *vs.* Normal control group; #*P*<0.05, ####*P*<0.0001 *vs.* Model control group
FIG. 1. Body Weight Changes of Each Group on Day 10.

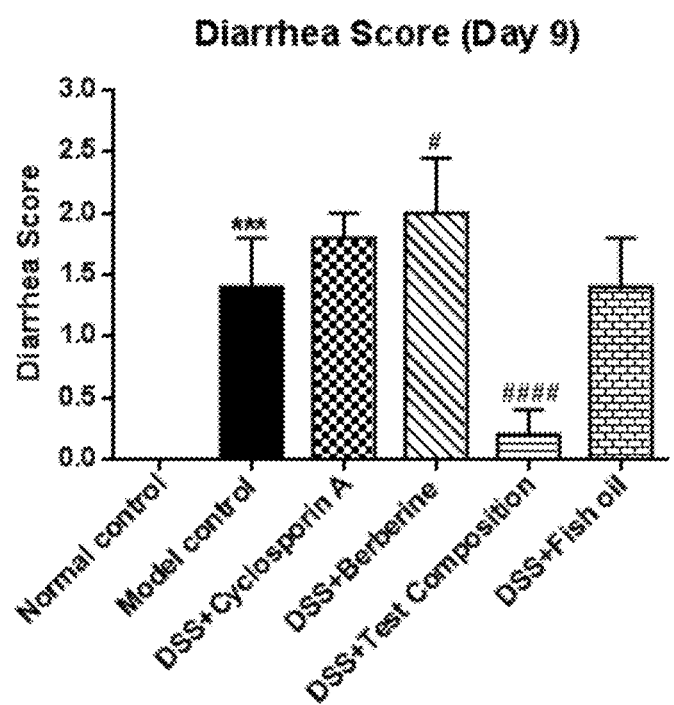
\*\*\* *P*<0.001 *vs.* Normal control group; #*P*<0.05, ####*P*<0.0001 *vs.* Model control group
FIG. 2. Diarrhea Scores of Each Group on Day 9.

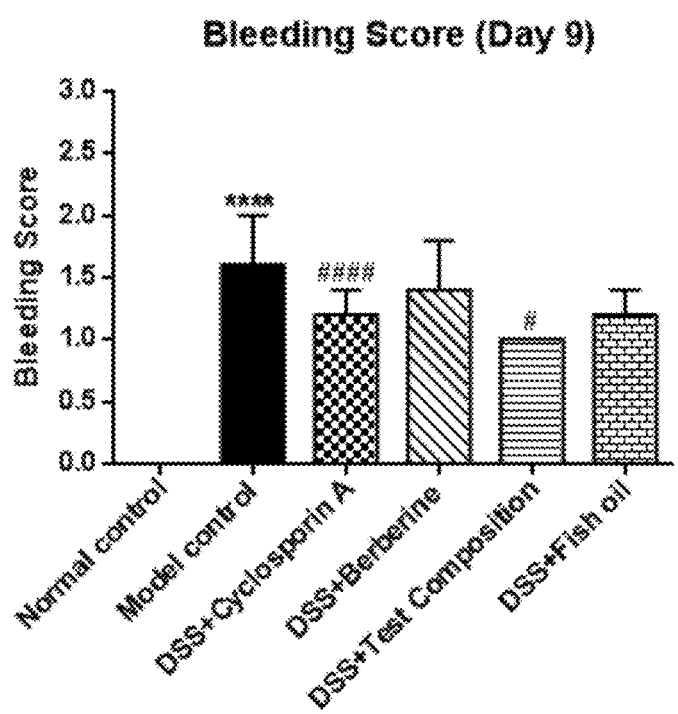
*** $P<0.001$ vs. Normal control group; #$P<0.05$, ####$P<0.0001$ vs. Model control group
FIG. 3. Bleeding Scores of Each Group on Day 9.

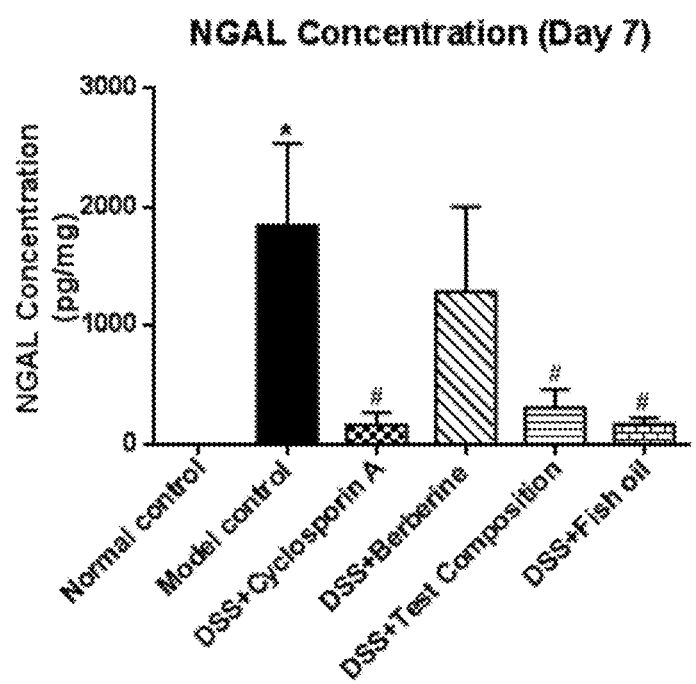
\* $P<0.05$ vs. Normal control group; #$P<0.05$ vs. Model control group
FIG. 4. NGAL Concentrations of Each Group on Day 7.

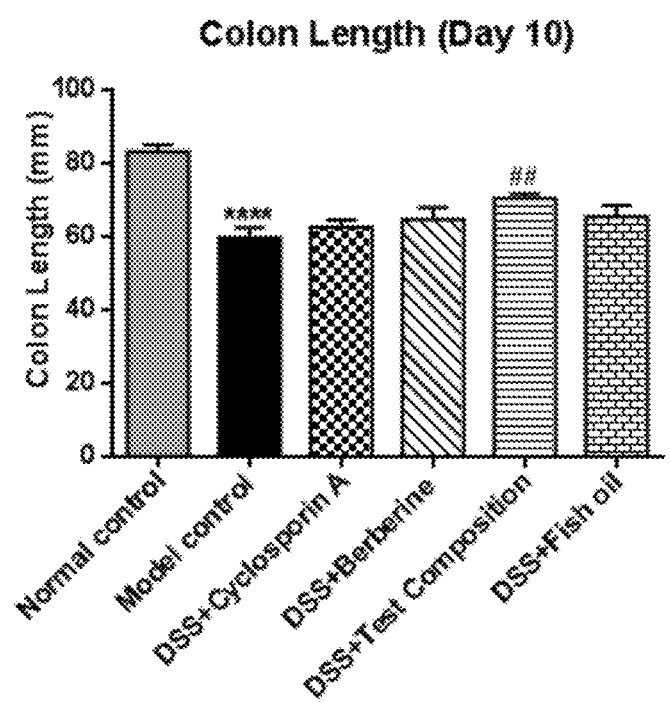
**** $P<0.0001$ vs. Normal control group; ##$P<0.01$ vs. Model control group
FIG. 5. Colon Length Data for Each Group.

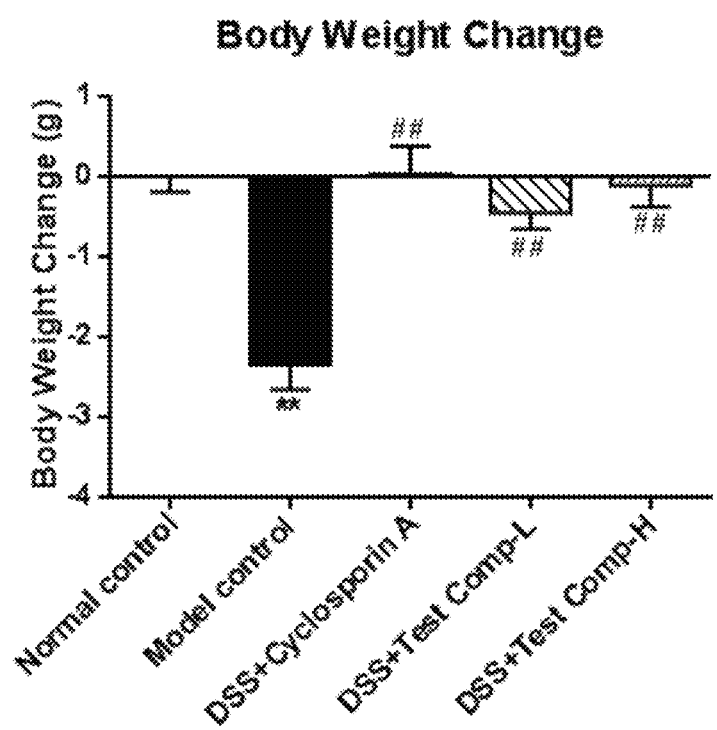
** $P<0.01$ vs. Normal control group; ##$P<0.01$ vs. Model control group
FIG. 6. Body Weight Changes of Each Group.

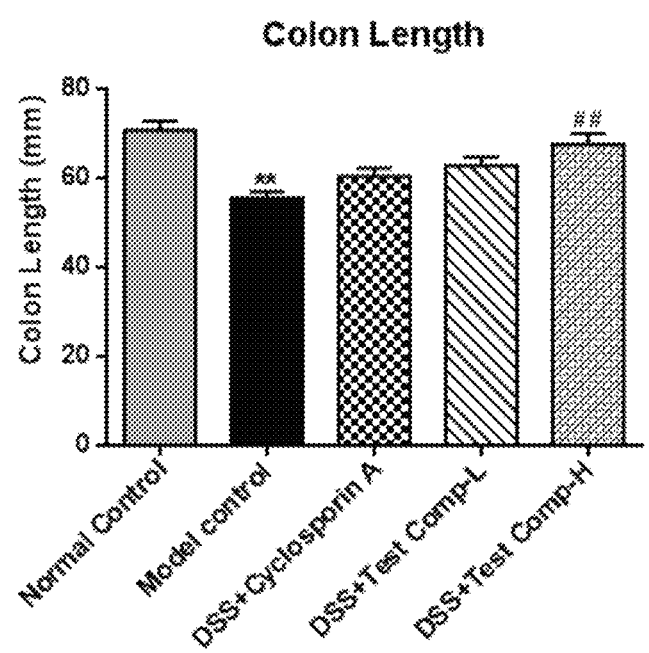
** $P<0.01$ vs. Normal control group; ##$P<0.01$ vs. Model control group
FIG. 7. Colon Length Data for Each Group.

METHODS AND COMPOSITIONS FOR TREATMENT OF INFLAMMATORY BOWEL DISEASE

This application is the U.S. national phase of and claims priority to PCT/CN2018/099425, filed Aug. 8, 2018, which claims the benefit of priority to U.S. Provisional Application No. 62/544,722, filed Aug. 11, 2017, the content of each of which is incorporated herein by reference in its entirety.

TECHNICAL FIELD OF THE INVENTION

The invention generally relates to pharmaceutical compositions and methods of therapeutic use thereof. In particular, the invention relates to novel pharmaceutical compositions of berberine or a derivative or analog of berberine, or a salt thereof, in combination with one or more omega-3 fatty acids, or esters thereof, and methods of their use in treating inflammatory bowel disease.

BACKGROUND OF THE INVENTION

Inflammatory bowel disease (IBD) involves chronic inflammation of all or part of the digestive tract. The two major forms of IBD are ulcerative colitis and Crohn's disease. In 2015, an estimated 1.3% of U.S. adults (~3 million) reported being diagnosed with either Crohn's disease or ulcerative colitis. (Dahlhamer et al. 2015 *Morbidity and Mortality Weekly Report* 65(42): 1166-1169.) There is also a continuing trend in the increased incidence and prevalence rates of IBD across Europe, Asia and Africa. (M'Koma 2013 *Clin Med Insights Gastroenterol.* 6:33-47.)

Ulcerative colitis causes long-lasting inflammation and ulcers in the innermost lining of the colon and rectum. Crohn's disease causes inflammation of the lining of the digestive tract. In Crohn's disease, inflammation often spreads deep into affected tissues. The inflammation can involve different areas of the digestive tract and can affect not only the small intestine and large intestine but also the mouth, esophagus, stomach and the anus. Both ulcerative colitis and Crohn's disease usually involve abdominal pain, vomiting, diarrhea, rectal bleeding, severe internal cramps/muscle spasms in the region of the pelvis, and weight loss. Inflamed colonic tissues express elevated levels of tumor necrosis factor alpha (TNFα) and other proinflammatory mediators, leading to tissue damage including apoptosis and loss of gut function. (Ngo et al. 2010 *Curr Mol Pharmacol.* 3(3): 145-52.)

Inflammatory bowel disease is a debilitating disease that is difficult to treat and can lead to life-threatening complications accompanied by high treatment cost to patients. (Park et al. 2010 *Inflamm Bowel Dis.* 17(7): 1603-9.) Current therapies for IBD are directed at interrupting inflammation rather than specifically promoting mucosal healing and include administration of anti-inflammatory and immunosuppressive drugs (e.g., mesalamine, corticosteroids, methotrexate, and infliximab). Such therapies have limited effect and are often associated with adverse side effects, such as nausea, vomiting, anorexia, fever, bone marrow suppression, etc. Despite availability of these medications, the therapeutics and methods currently available for IBD are suboptimal. (Rutgeerts et al. 2009 *Gastroenterology* 136(4): 1182-97.)

There remains an ongoing and urgent need for novel and improved therapeutics and methods for treating IBD and related diseases or disorders.

SUMMARY OF THE INVENTION

The invention is based in part on the unexpected discovery of methods for treating IBD using berberine or a derivative or analog of berberine, or a salt thereof, in specifically designed combinations with one or more omega-3 fatty acids or esters thereof. The methods and pharmaceutical compositions of the invention can be utilized to treat various types of IBD, e.g., ulcerative colitis and Crohn's disease, or related diseases or disorders.

In one aspect, the invention generally relates to a method for treating, reducing, or preventing inflammatory bowel disease or a related disease or disorder. The method includes: administering to a subject in need thereof a therapeutically effective amount of a pharmaceutical composition comprising berberine or a derivative or analog of berberine, or a pharmaceutically acceptable salt thereof, and one or more omega-3 fatty acids, or esters thereof, and optionally a pharmaceutically acceptable excipient, carrier or diluent.

In another aspect, the invention generally relates to use of berberine or a derivative or analog of berberine, or a pharmaceutically acceptable salt thereof, and one or more omega-3 fatty acids, or esters thereof, and optionally one or more pharmaceutically acceptable excipient, carrier or diluent, in preparation of a medicament for treating inflammatory bowel disease, or a related disease or disorder, in a mammal in need thereof.

In yet another aspect, the invention generally relates to a pharmaceutical composition for treating inflammatory bowel disease, or a related disease or condition. The pharmaceutical composition includes: berberine or a derivative or analog of berberine, or a pharmaceutically acceptable salt thereof; one or more omega-3 fatty acids, or a pharmaceutically acceptable ester thereof, each being present in an amount that, when administered to a subject, is sufficient to treat inflammatory bowel disease, or a related disease or condition in a mammal, including a human.

In yet another aspect, the invention generally relates to a unit dosage form comprised of a pharmaceutical composition or medicament disclosed herein.

In yet another aspect, the invention generally relates to a kit that includes: (i) berberine or a derivative or analog of berberine, or a pharmaceutically acceptable salt thereof; (ii) one or more omega-3 fatty acids, or esters thereof; (iii) optionally one or more agent(s) selected from the group consisting of vitamin D, vitamin A, vitamin C, vitamin E, vitamin B, vitamin K, and calcium; and instructions for administering agents (i), (ii) and (iii) to a patient having inflammatory bowel disease or a related disease or condition.

BRIEF DESCRIPTION OF THE DRAWINGS

FIG. 1 shows certain exemplary data on body weight changes.

FIG. 2 shows certain exemplary data on diarrhea scores.

FIG. 3 shows certain exemplary data on bleeding scores.

FIG. 4 shows certain exemplary data on NGAL concentrations.

FIG. 5 shows certain exemplary data on colon length.

FIG. 6 shows certain exemplary data on body weight changes.

FIG. 7 shows certain exemplary data on colon length.

Definitions

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

It will be appreciated that the compounds, as described herein, may be substituted with any number of substituents or functional moieties. Throughout the specifications, groups and substituents thereof may be chosen to provide stable moieties and compounds.

As used herein, the terms "effective amount" or "therapeutically effective amount" of an active agent refer to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the term "treating, reducing, or preventing a disease or disorder" refers to ameliorating such a condition before or after it has occurred. As compared with an equivalent untreated control, such reduction or degree of prevention is at least 5%, 10%, 20%, 40%, 50%, 60%, 80%, 90%, 95%, or 100% as measured by any standard technique.

As used herein, the term "pharmaceutically acceptable salt" refers to either a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

As used herein, the term "pharmaceutically acceptable excipient, carrier, or diluent" refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the terms "isolated" or "purified" refer to a material that is substantially or essentially free from components that normally accompany it in its native state. Purity and homogeneity are typically determined using analytical chemistry techniques such as polyacrylamide gel electrophoresis or high performance liquid chromatography.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

As used herein, the "an amount sufficient" refers to the amount of a compound, alone or in combination with another therapeutic regimen, required to treat, prevent, or reduce a disease or disorder in a clinically relevant manner. A sufficient amount of an active compound used to practice the present invention for therapeutic treatment of conditions caused by or contributing to diabetes varies depending upon the manner of administration, the age, body weight, and general health of the mammal or patient. Ultimately, the prescribers will decide the appropriate amount and dosage regimen. Additionally, an effective amount may be an amount of compound in the combination of the invention that is safe and efficacious in the treatment of a patient having a metabolic disorder such as diabetes over each agent alone as determined and approved by a regulatory authority (such as the U.S. Food and Drug Administration).

As used herein, the "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that reduces glucose levels and that is formulated for administration by inhalation will differ from a low dosage of the same agent formulated for oral administration.

As used herein, the "high dosage" is meant at least 5% (e.g., at least 10%, 20%, 50%, 100%, 200%, or even 300%) more than the highest standard recommended dosage of a particular compound for treatment of any human disease or condition.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements, and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^1H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. See, WO 2007/005643, WO 2007/005644, WO 2007/016361, and WO 2007/016431.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound.

DETAILED DESCRIPTION OF THE INVENTION

The invention provides various novel compositions of berberine or a derivative or analog of berberine, or a salt thereof, in combination with one or more omega-3 fatty acids, e.g., eicosapentaenoic acid (EPA) and docosahexaenoic acid (DHA), or esters thereof, and methods of their use in treating, reducing and/or preventing inflammatory bowel disease, e.g., ulcerative colitis and Crohn's disease, or related diseases or disorders.

Key features of the invention include the synergistic pharmacological effects and reduction of side effects given rise by the selective combinations of the key agents: (1) berberine or a derivative or analog of berberine, or a salt thereof, which increases the bioavailability and reduces the risk of certain side effects of omega-3 fatty acids, or esters thereof, (2) omega-3 fatty acids (e.g., EPA and/or DHA), or esters thereof, which significantly improves the bioavailability and reduces the risk of undesirable side effects of berberine or a derivative or analog of berberine, or a salt thereof, and (3) specific ratios and dosages of these agents to optimize the desired therapeutic effect while minimizing the respective side effects.

Berberine (5,6-dihydro-9,10-dimethoxybenzo[g]-1,3-benzodioxolo[5,6-a]quinolizinium), is an isoquinoline alkaloid isolated from Rhizoma Coptidis. Berberine is found in a variety of plants as *Berberis, Hydrastis canadensis, Xanthorhiza simplicissima, Phellodendron amurense, Coptis chinensis, Tinospora cordifolia, Argemone mexicana*, and *Eschscholzia californica*.

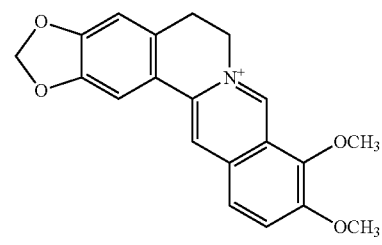

Berberine

Currently, berberine can be obtained commercially in the form of chloride, sulfate or tannate salt, with berberine chloride having been used in almost all previous studies.

Omega-3 fatty acids (a.k.a. ω-3 fatty acids or n-3 fatty acids) are polyunsaturated fatty acids (PUFAs) with a double bond (C=C) at the third carbon atom from the end of the carbon chain. The three types of omega-3 fatty acids involved in human physiology are α-linolenic acid (ALA), which is found in plant oils, and EPA and DHA, both of which are commonly found in oils of marine organisms. Marine fish, algae and phytoplankton are primary sources of omega-3 fatty acids. Fish oil refers to oils derived from the tissues of oily fish. Fish oils contain omega-3 fatty acids such as EPA and DHA.

EPA is the active molecule in three FDA-approved antihypertriglyceridemic agents. In addition to EPA and DHA, many more omega-3 fatty acids existed in nature with a range of therapeutic benefits, include but not limited to Docosapentaenoic acid (DPA), α-Linolenic acid (ALA), Eicosatrienoic acid (ETE), etc.

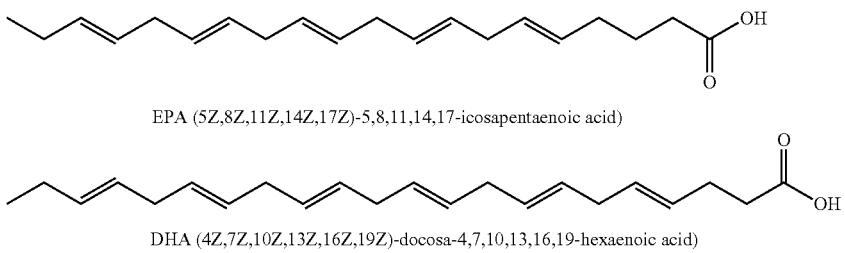

EPA (5Z,8Z,11Z,14Z,17Z)-5,8,11,14,17-icosapentaenoic acid

DHA (4Z,7Z,10Z,13Z,16Z,19Z)-docosa-4,7,10,13,16,19-hexaenoic acid

Other omega-3 fatty acids may also be used here in addition to or in place of one or both of EPA and DHA, for example, docosapentaenoic acid, α-Linolenic acid, eicosatrienoic acid, hexadecatrienoic acid, stearidonic acid, eicosatetraenoic acid, heneicosapentaenoic acid, tetracosapentaenoic acid and tetracosahexaenoic acid.

In one aspect, the invention generally relates to a method for treating, reducing, or preventing inflammatory bowel disease, or a related disease or disorder. The method includes: administering to a subject in need thereof a therapeutically effective amount of a pharmaceutical composition comprising berberine or a derivative or analog of berberine, or a pharmaceutically acceptable salt thereof, and one or more omega-3 fatty acids, or esters thereof, and optionally a pharmaceutically acceptable excipient, carrier or diluent.

Any suitable derivative or analog may be employed. Table 1 lists certain exemplary derivatives and analogs of berberine.

TABLE 1

Exemplary Berberine Derivatives or Analogs

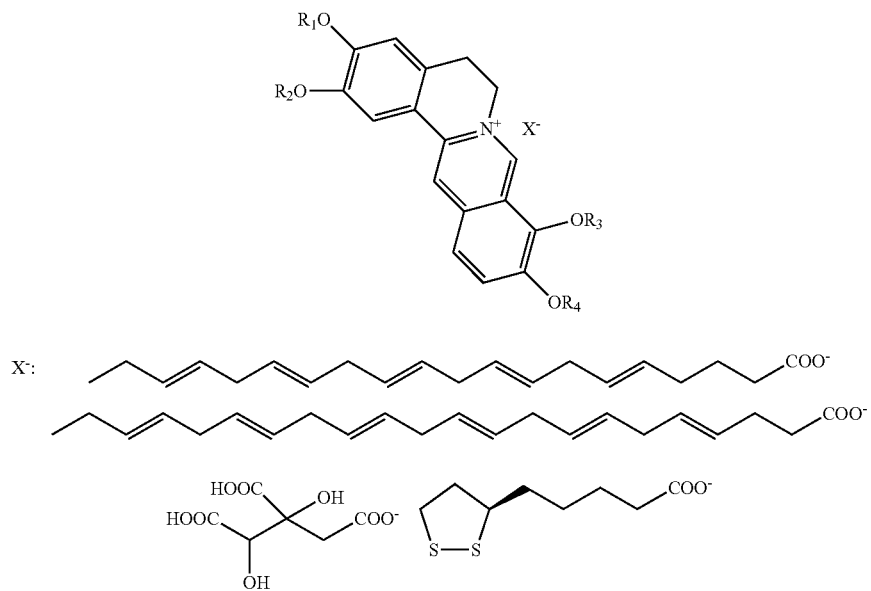

TABLE 1-continued
Exemplary Berberine Derivatives or Analogs
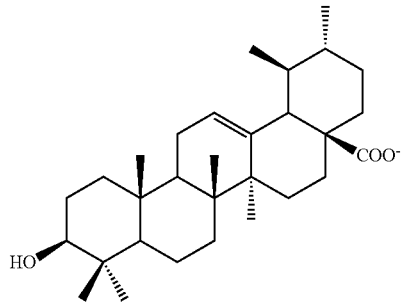
$R_1 = R_2 = R_3 = R_4 = CH_3$
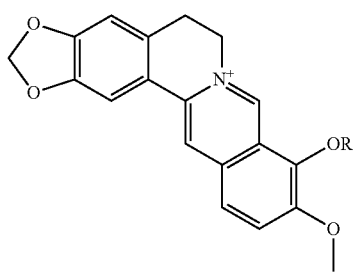
R = H
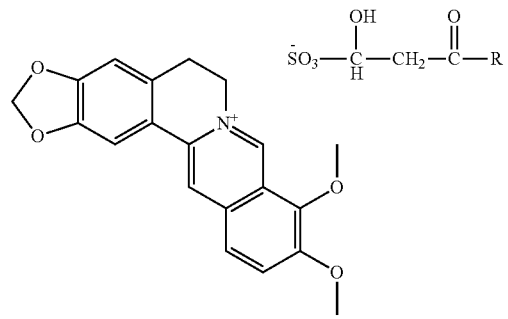
R = $C_8$-$C_{12}$ alkyl
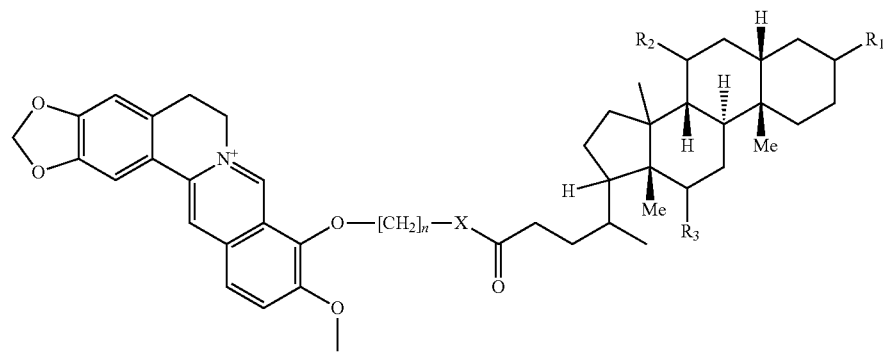
$R_1$ = OH, carbonyl; $R_2$, $R_3$ = H, carbonyl; n = 2-6; X = O
$R_1$ = OH, carbonyl; $R_2$, $R_3$ = H, OH, carbonyl; n = 2-6; X = NH TABLE 1-continued Exemplary Berberine Derivatives or Analogs

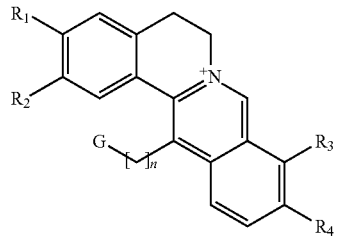

$R_1, R_3, R_2, R_4$ = OH, $C_1$-$C_6$ alkoxy, $OCH_2O$
G = Z—Ar, Y—$Ar_2$
Z = $O(CH_2)_m$, $CONH(CH_2)_m$, $NHCO(CH_2)_m$
Y = $O(CH_2)_mCH$, $CONH(CH_2)_mCH$, $NHCO(CH_2)_mCH$
n = 1-5; m = 1-3; Ar = 5-15 membered unsaturated or aromatic ring

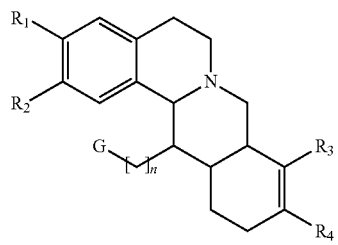

$R_1, R_3, R_2, R_4$ = OH, $C_1$-$C_6$ alkoxy, $OCH_2O$
G = Z—Ar, Y—$Ar_2$
Z = $O(CH_2)_m$, $CONH(CH_2)_m$, $NHCO(CH_2)_m$
Y = $O(CH_2)_mCH$, $CONH(CH_2)_mCH$, $NHCO(CH_2)_mCH$
n = 1-5; m = 1-3; Ar = 5-15 membered unsaturated or aromatic ring

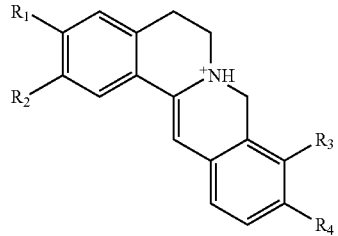

$R_1, R_3, R_2, R_4$ = OH, $C_1$-$C_6$ alkoxy, $OCH_2O$
G = Z—Ar, Y—$Ar_2$
Z = $O(CH_2)_m$, $CONH(CH_2)_m$, $NHCO(CH_2)_m$
Y = $O(CH_2)_mCH$, $CONH(CH_2)_mCH$, $NHCO(CH_2)_mCH$
n = 1-5; m = 1-3; Ar = 5-15 membered unsaturated or aromatic ring TABLE 1-continued Exemplary Berberine Derivatives or Analogs

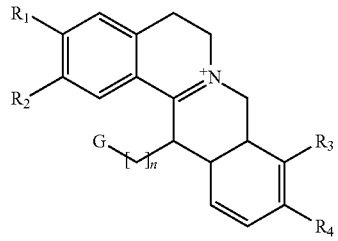

$R_1$, $R_3$, $R_2$, $R_4$ = OH, $C_1$-$C_6$ alkoxy, $OCH_2O$
G = Z—Ar, Y—$Ar_2$
Z = $O(CH_2)_m$, $CONH(CH_2)_m$, $NHCO(CH_2)_m$
Y = $O(CH_2)_mCH$, $CONH(CH_2)_mCH$, $NHCO(CH_2)_mCH$
n = 1-5; m = 1-3; Ar = 5-15 membered unsaturated or aromatic ring

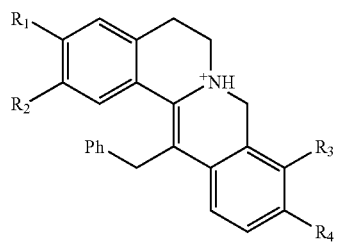

$R_1$, $R_3$, $R_2$, $R_4$ = OH, $C_1$-$C_6$ alkoxy, $OCH_2O$
G = Z—Ar, Y—$Ar_2$
Z = $O(CH_2)_m$, $CONH(CH_2)_m$, $NHCO(CH_2)_m$
Y = $O(CH_2)_mCH$, $CONH(CH_2)_mCH$, $NHCO(CH_2)_mCH$
n = 1-5; m = 1-3; Ar = 5-15 membered unsaturated or aromatic ring

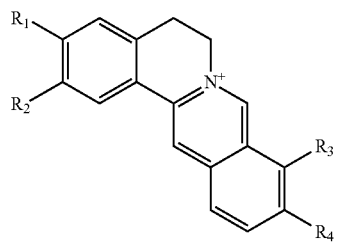

$R_1$, $R_2$, $R_3$, $R_4$ = $OCH_3$, OH, $OCH_2O$

TABLE 1-continued
Exemplary Berberine Derivatives or Analogs
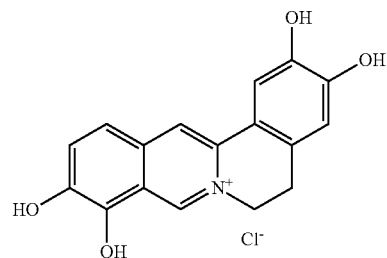 [SMILES: Oc1cc2c(cc1O)-c1cc3ccc(O)c(O)c3c[n+]1CC2 ; [Cl-]]
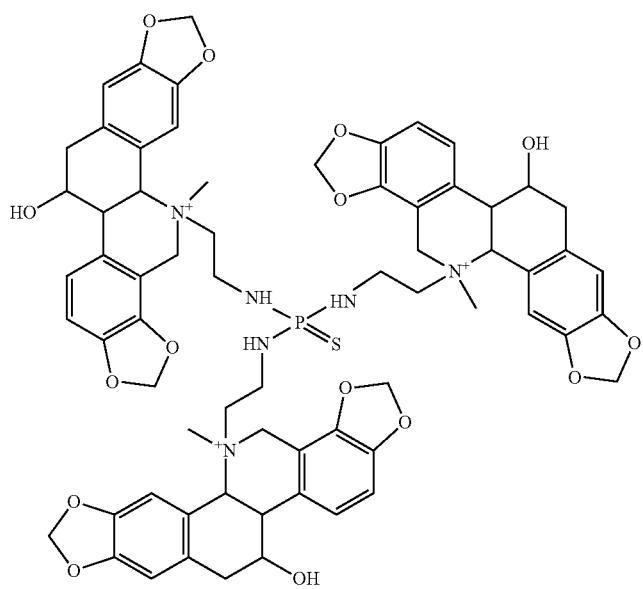 [SMILES: C[N+]1(CCNP(=S)(NCC[N+]2(C)Cc3c(ccc4c3OCO4)C3C(O)Cc4cc5c(cc4C32)OCO5)NCC[N+]2(C)Cc3c(ccc4c3OCO4)C3C(O)Cc4cc5c(cc4C32)OCO5)Cc2c(ccc3c2OCO3)C2C(O)Cc3cc4c(cc3C21)OCO4]
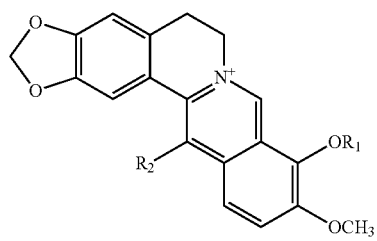
R₁ = H, Me
R₂ = Bn, 3,5-dinitrobenzyl
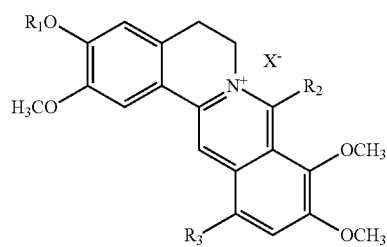
X = F, Cl, Br, I, SO₄, NO₃, PO₄, citrate,
acetate, lactate
R₁ and R₂ = independently alkyl; R₃ =
H, F, Cl, Br, or I TABLE 1-continued
Exemplary Berberine Derivatives or Analogs
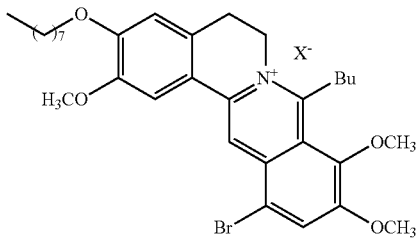
X = F, Cl, Br, I, SO$_4$, NO$_3$, PO$_4$, citrate, acetate, lactate
R$_1$ and R$_2$ = independently alkyl; R$_3$ = H, F, Cl, Br, or I
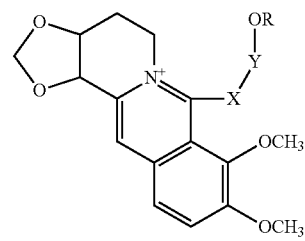
Y = CH$_2$, —C═O, —C═S;
X = C having a linear, branched, saturated/unsaturated linear structure; n = 1-10
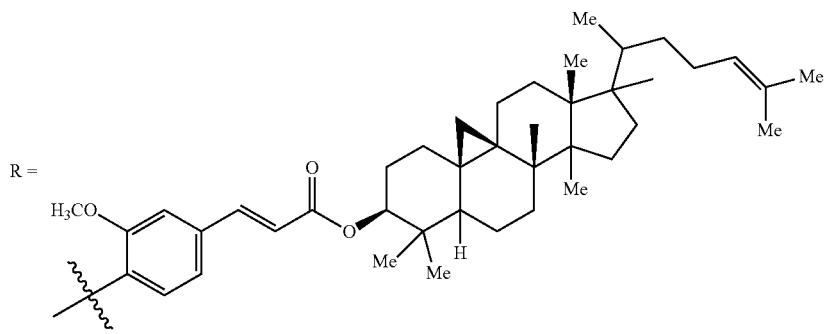
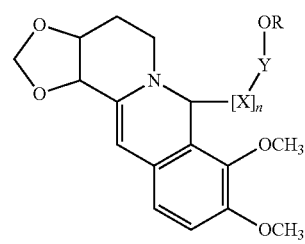
Y = CH$_2$, —C═O, —C═S;
X = C having a linear, branched, saturated/unsaturated linear structure; n = 1-10

TABLE 1-continued
Exemplary Berberine Derivatives or Analogs
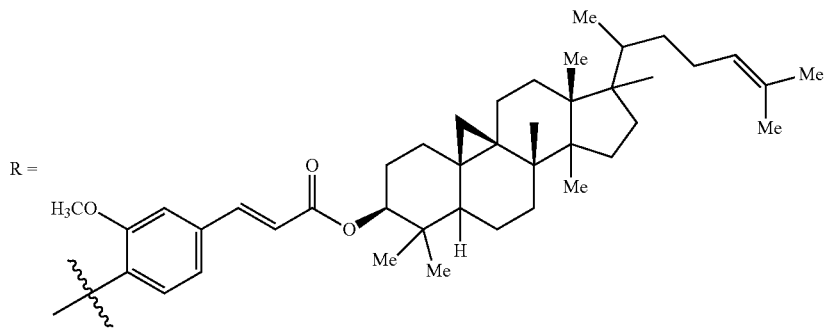
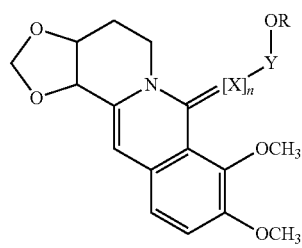
Y = CH₂, —C═O, —C≡S;
X = C having a linear, branched,
saturated/unsaturated linear
structure; n = 1-10
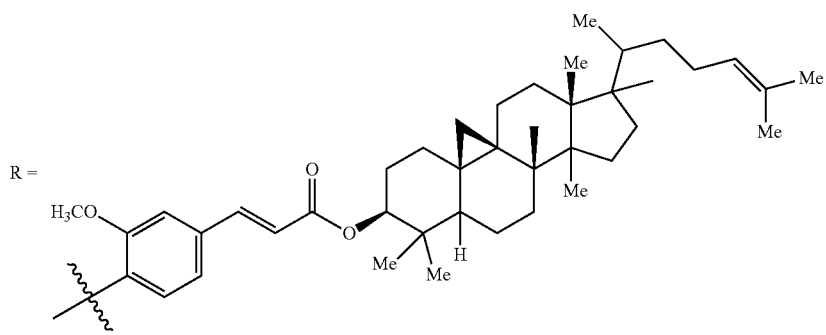
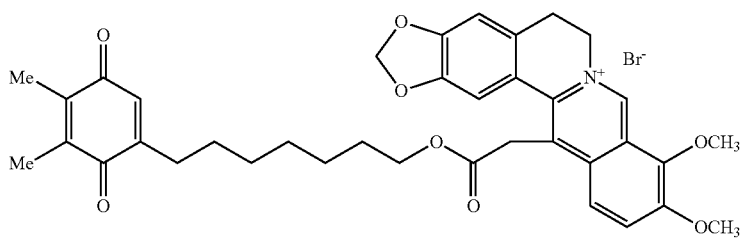 [SMILES: COc1ccc2c(CC(=O)OCCCCCCCC3=CC(=O)C(C)=C(C)C3=O)c3[n+](cc2c1OC)CCc1cc2c(cc1-3)OCO2 ; [Br-]]
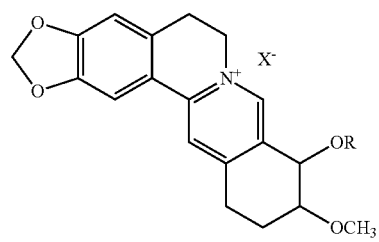
R = glucosyl, mannosyl, maltosyl, lactosyl,
galactosyl, fructosyl, xylosyl, arabinosyl
X = Cl, Br, I TABLE 1-continued
Exemplary Berberine Derivatives or Analogs
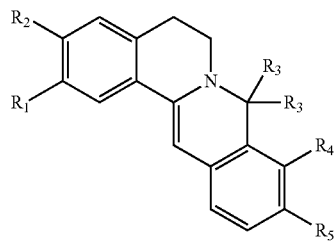
R$_1$, R$_2$ = H, C$_1$-C$_4$ alkoxy, OCH$_2$O
R$_3$ = C$_1$-C$_3$ alkyl
R$_4$, R$_5$ = C$_1$-C$_2$ alkoxy
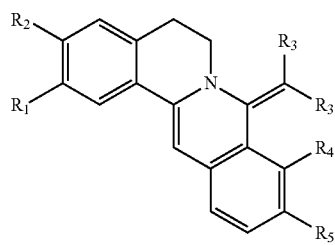
R$_1$, R$_2$ = H, C$_1$-C$_4$ alkoxy, OCH$_2$O
R$_3$ = CN, COOR$_6$ (R$_6$ = C$_1$-C$_2$ alkyl)
R$_4$, R$_5$ = C$_1$-C$_2$ alkoxy
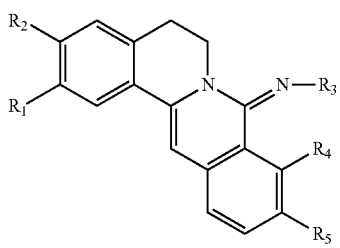
R$_1$, R$_2$ = H, C$_1$-C$_4$ alkoxy, OCH$_2$O
R$_3$ = C$_1$-C$_2$ alkyl, phenyl
R$_4$, R$_5$ = C$_1$-C$_2$ alkoxy TABLE 1-continued Exemplary Berberine Derivatives or Analogs

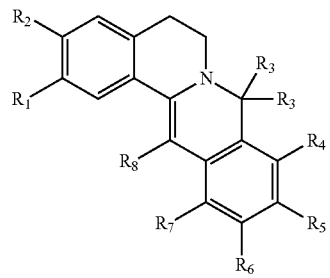

$R_1, R_2 = H, (CH_2)_{0-6}CO_2R', C(O)R'',$
$OR', NR_{10}R_{11}, C(O)NR_{10}R_{11},$ alkyl
$R_1R_2 = OCH_2CH_2O; R_8, R_8 = H,$
OH, Cl, Br, F, I, CN, $NH_2$, $(O)NH_2$,
$CO_2H$, alkyl; $R_3' = H; R_5R_3' = O;$
$R_4 = H$, halogen, $OR', OSO_2R'',$
$OC(O)R'', OCO2R'' OC(O)NR'R'',$
O-alkylene-NR'R'', O-alkylene-
$OSO_2R''$, O-alkylene-NR'$SO_2R''$,
O-alkylene-NR'COR', alkyl;
$R_5, R_6 = H$, halogen, OH, alkoxy
$R_4R_5 = OCH_2O; R_5R_6 = OCH_2O;$
$R_7 = H$, OH, halogen, alkyl or alkoxy
$R_{10}, R_{11} = H, CO_2R''$, alkyl

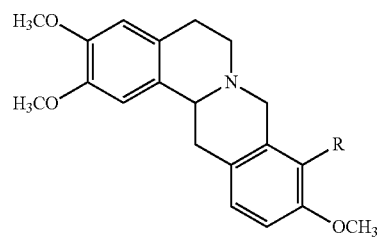

$R = SO_2C_6H_4$-3-F

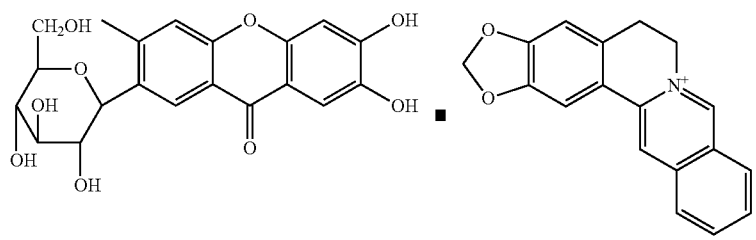

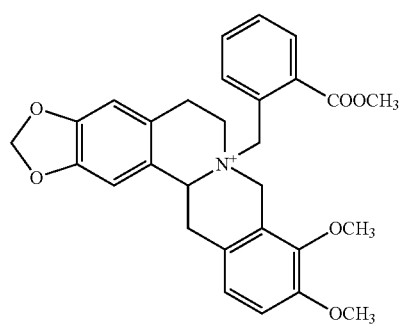 [SMILES: COC(=O)c1ccccc1C[N+]12CCc3cc4c(cc3C1Cc1ccc(OC)c(OC)c1C2)OCO4]

TABLE 1-continued
Exemplary Berberine Derivatives or Analogs
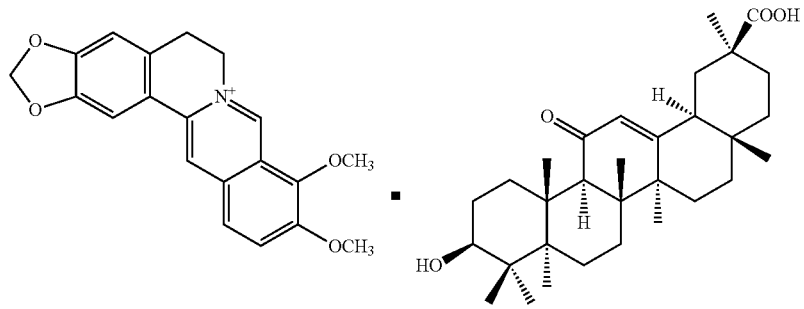
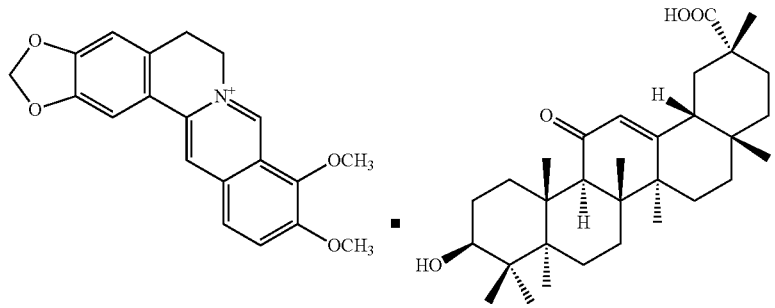
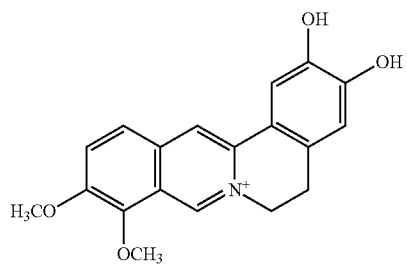
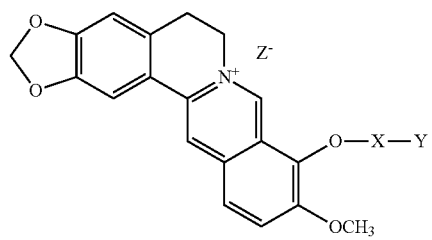
X = (CH$_2$)$_n$, (CH$_2$)$_m$CO, n = 2-10; m = 1-9
Y = NR$_1$Ar, OAr; Ar = substituted aryl
R$_1$ = H, Me, Et, Pr, i-Pr; Z = F, Cl, Br, I
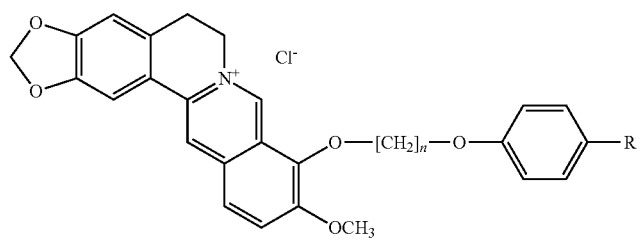
R = 2-acetic acid Me ester, 3-acetic Me ester, 4-acetic Me ester, 2-acetic Me Et ester, 3-acetic Me Et ester, 4-acetic Me Et ester, 2-acetate, 3-acetate, 4-acetate, 2-acetate potassium, 3-acetate potassium, 4-acetate potassium; n = 2-6

In certain embodiments, the pharmaceutically acceptable salt of berberine or a derivative or analog of berberine may be selected from salts of berberine cation or a cation of a derivative or analog of berberine, with anions of chloride, bromide, iodide, sulfate, bisulfate, hemisulphate, nitrate, phosphate, acid phosphate, isonicotinate, acetate, lactate, salicylate, citrate, tartrate, pantothenate, bitartrate, ascorbate, succinate, tannate, maleate, gentisinate, fumarate, gluconate, glucaronate, saccharate, formate, benzoate, glutamate, etc. Berberine and its pharmaceutically acceptable salt form are sometimes singly or collectively referred to herein as "BBR".

In certain embodiments of the method, the pharmaceutical composition includes eicosapentaenoic acid, or a pharmaceutically acceptable ester thereof.

In certain embodiments of the method, the pharmaceutical composition includes docosahexaenoic acid, or a pharmaceutically acceptable ester thereof.

In certain embodiments of the method, the pharmaceutical composition includes only one omega-3 fatty acid, or a pharmaceutically acceptable ester thereof. In certain embodiments of the method, the pharmaceutical composition includes two or more omega-3 fatty acids, or pharmaceutically acceptable esters thereof.

In certain embodiments of the method, the pharmaceutical composition includes eicosapentaenoic acid, or an ester thereof, and docosahexaenoic acid, or an ester thereof.

In certain embodiments of the method, the pharmaceutical composition includes an ester (e.g., ethyl ester) of eicosapentaenoic acid and docosahexaenoic acid.

In certain embodiments of the method, the pharmaceutical composition includes eicosapentaenoic acid and an ester (e.g., ethyl ester) of docosahexaenoic acid.

In certain embodiments of the method, the pharmaceutical composition includes eicosapentaenoic acid and docosahexaenoic acid.

In certain embodiments of the method, the pharmaceutical composition includes an ester (e.g., ethyl ester) of eicosapentaenoic acid and an ester (e.g., ethyl ester) of docosahexaenoic acid.

In certain embodiments of the method, the weight ratio of eicosapentaenoic acid, or an ester thereof, and docosahexaenoic acid, or an ester thereof, is from about 1:1,000 to about 1,000:1 (e.g., from about 1:500 to about 500:1, from about 1:100 to about 100:1, from about 1:50 to about 50:1, from about 1:20 to about 20:1, from about 1:10 to about 10:1, from about 1:5 to about 5:1, from about 1:3 to about 3:1, from about 1:2 to about 2:1, about 1:1).

In certain embodiments of the method, the weight ratio of berberine or a derivative or analog of berberine, or a pharmaceutically acceptable salt thereof, to the one or more omega-3 fatty acids, or esters thereof, is from about 10:1 to about 1:20 (e.g., from about 7:1 to about 1:20, from about 5:1 to about 1:20, from about 3:1 to about 1:20, from about 1:1 to about 1:20, from about 10:1 to about 1:15, from about 10:1 to about 1:12, from about 10:1 to about 1:10, from about 10:1 to about 1:8, from about 10:1 to about 1:5, from about 10:1 to about 1:3, from about 10:1 to about 1:1, from about 5:1 to about 1:10, from about 3:1 to about 1:10, from about 1:1 to about 1:10, from about 5:1 to about 1:5, from about 5:1 to about 1:3, from about 5:1 to about 1:1, from about 10:1 to about 5:1, from about 10:1 to about 6:1, from about 10:1 to about 7:1, from about 1:10 to about 1:20, from about 1:10 to about 1:15).

In certain embodiments, the pharmaceutical composition includes berberine, or a pharmaceutically acceptable salt thereof, and one or more omega-3 fatty acids at a weight ratio (e.g., BBR to EPA/DHA) from about 10:1 to about 1:20 (e.g., from about 7:1 to about 1:20, from about 5:1 to about 1:20, from about 3:1 to about 1:20, from about 1:1 to about 1:20, from about 10:1 to about 1:15, from about 10:1 to about 1:12, from about 10:1 to about 1:10, from about 10:1 to about 1:8, from about 10:1 to about 1:5, from about 10:1 to about 1:3, from about 10:1 to about 1:1, from about 5:1 to about 1:10, from about 3:1 to about 1:10, from about 1:1 to about 1:10, from about 5:1 to about 1:5, from about 5:1 to about 1:3, from about 5:1 to about 1:1, from about 10:1 to about 5:1, from about 10:1 to about 6:1, from about 10:1 to about 7:1, from about 1:10 to about 1:20, from about 1:10 to about 1:15).

In certain embodiments of the method, the pharmaceutical composition further comprises one or more agents selected from the group consisting of vitamin D, vitamin A, vitamin C, vitamin E, vitamin B, vitamin K, and calcium.

In certain embodiments of the method, the pharmaceutical composition comprises vitamin D.

In certain embodiments of the method, the one or more omega-3 fatty acids, or esters thereof, are provided as components of a fish oil.

In certain embodiments of the method, the fish oil is derived from tissues of oily fish, which has about 10% to about 100% omega-3 fatty acids, or esters thereof.

Any suitable salt of berberine or a derivative or analog of berberine may be employed. In certain embodiments of the method, the pharmaceutically acceptable salt of berberine or a derivative or analog of berberine is a chloride salt. In certain embodiments of the method, the pharmaceutically acceptable salt of berberine or a derivative or analog of berberine is a sulfate salt.

Any suitable esters of omega-3 fatty acids may be employed. As used herein, the term "pharmaceutically acceptable ester," refers to esters that hydrolyze in vivo and include those that break down readily in the human body to leave the parent compound or a salt thereof. Examples of particular esters include esters formed by an acid with a substituted or unsubstituted aliphatic alcohol (R—OH, wherein R is an alkyl group), for example, $C_1$-$C_6$ alkyl esters of eicosapentaenoic acid and of docosahexaenoic acid. Examples of $C_1$-$C_6$ alkyl esters include ethyl esters, propyl esters and butyl esters.

In certain embodiments of the method, the subject is administered a unit dosage form having about 9 mg to about 300 mg (e.g., about 9 mg to about 250 mg, about 9 mg to about 200 mg, about 9 mg to about 150 mg, about 9 mg to about 100 mg, about 9 mg to about 75 mg, about 9 mg to about 50 mg, about 9 mg to about 25 mg, about 12.5 mg to about 300 mg, about 25 mg to about 300 mg, about 50 mg to about 300 mg, about 100 mg to about 300 mg, about 150 mg to about 300 mg, about 100 mg to about 300 mg) of berberine or a derivative or analog of berberine, or a pharmaceutically acceptable salt thereof, and about 3 mg to about 2,400 mg (e.g., about 3 mg to about 1,800 mg, about 3 mg to about 1,200 mg, about 3 mg to about 900 mg, about 3 mg to about 600 mg, about 3 mg to about 500 mg, about 3 mg to about 250 mg, about 3 mg to about 100 mg, about 3 mg to about 75 mg, about 3 mg to about 50 mg, about 3 mg to about 25 mg, about 3 mg to about 12.5 mg, about 6 mg to about 2,400 mg, about 9 mg to about 2,400 mg, about 12.5 mg to about 2,400 mg, about 25 mg to about 2,400 mg, about 50 mg to about 2,400 mg, about 100 mg to about 2,400 mg, about 250 mg to about 2,400 mg, about 500 mg to about 2,400 mg, about 1,000 mg to about 2,400 mg, about 1,500 mg to about 2,400 mg) of the one or more omega-3 fatty acids, or pharmaceutically acceptable esters thereof.

In certain embodiments of the method, the subject is administered a unit dosage form having about 9 mg to about 300 mg (e.g., about 9 mg to about 250 mg, about 9 mg to about 200 mg, about 9 mg to about 150 mg, about 9 mg to about 100 mg, about 9 mg to about 75 mg, about 9 mg to about 50 mg, about 9 mg to about 25 mg, about 12.5 mg to about 300 mg, about 25 mg to about 300 mg, about 50 mg to about 300 mg, about 100 mg to about 300 mg, about 150 mg to about 300 mg, about 100 mg to about 300 mg) of berberine, or a pharmaceutically acceptable salt thereof, and about 3 mg to about 2,400 mg (e.g., about 3 mg to about 1,800 mg, about 3 mg to about 1,200 mg, about 3 mg to about 900 mg, about 3 mg to about 600 mg, about 3 mg to about 500 mg, about 3 mg to about 250 mg, about 3 mg to about 100 mg, about 3 mg to about 75 mg, about 3 mg to about 50 mg, about 3 mg to about 25 mg, about 3 mg to about 12.5 mg, about 6 mg to about 2,400 mg, about 9 mg to about 2,400 mg, about 12.5 mg to about 2,400 mg, about 25 mg to about 2,400 mg, about 50 mg to about 2,400 mg, about 100 mg to about 2,400 mg, about 250 mg to about 2,400 mg, about 500 mg to about 2,400 mg, about 1,000 mg to about 2,400 mg, about 1,500 mg to about 2,400 mg) of the one or more omega-3 fatty acids, or pharmaceutically acceptable esters thereof.

In certain embodiments of the method, the pharmaceutical composition is in the form of a soft gel capsule.

In certain embodiments of the method, the pharmaceutical composition is in the form of a tablet.

In certain embodiments of the method, the pharmaceutical composition is in the form of a liquid solution or suspension.

In certain embodiments of the method, the soft gel capsule, tablet, or liquid solution or suspension is administered from once, twice or three times daily.

A subject may be administered of the pharmaceutical composition daily for a period from about one day to 3 days, 7 days, 14 days, 1 month, 2 months, 3 months, six months, or one year, or a time shorter or longer thereof as deemed necessary.

In certain embodiments, the method is used to treat a subject having ulcerative colitis.

In certain embodiments, the method is used to treat a subject having Crohn's disease.

In certain embodiments, the method is used to treat a subject having both ulcerative colitis and Crohn's disease.

In certain embodiments, the method is used to treat a subject having acute inflammatory bowel disease (e.g., ulcerative colitis and/or Crohn's disease).

In certain embodiments, the method is used to treat a subject having chronic inflammatory bowel disease (e.g., ulcerative colitis and/or Crohn's disease).

In another aspect, the invention generally relates to use of berberine or a derivative or analog of berberine, or a pharmaceutically acceptable salt thereof, and one or more omega-3 fatty acids, or esters thereof, and optionally one or more pharmaceutically acceptable excipient, carrier or diluent, in preparation of a medicament for treating inflammatory bowel disease, or a related disease or disorder, in a mammal in need thereof.

In certain embodiments of the use, the medicament includes eicosapentaenoic acid, or a pharmaceutically acceptable ester thereof.

In certain embodiments of the use, the medicament includes docosahexaenoic acid, or a pharmaceutically acceptable ester thereof.

In certain embodiments of the method, the pharmaceutical composition includes only one omega-3 fatty acid, or a pharmaceutically acceptable ester thereof. In certain embodiments of the method, the pharmaceutical composition includes two or more omega-3 fatty acids, or pharmaceutically acceptable esters thereof.

In certain embodiments of the use, the medicament includes eicosapentaenoic acid, or an ester thereof, and docosahexaenoic acid, or an ester thereof.

In certain embodiments of the use, the medicament includes an ester (e.g., ethyl ester) of eicosapentaenoic acid and docosahexaenoic acid.

In certain embodiments of the use, the medicament includes eicosapentaenoic acid and an ester (e.g., ethyl ester) of docosahexaenoic acid.

In certain embodiments of the use, the medicament includes eicosapentaenoic acid and docosahexaenoic acid.

In certain embodiments of the use, the medicament includes an ester (e.g., ethyl ester) of eicosapentaenoic acid and an ester (e.g., ethyl ester) of docosahexaenoic acid.

In certain embodiments of the use, the weight ratio of eicosapentaenoic acid, or an ester thereof, and docosahexaenoic acid, or an ester thereof, is from about 1:1,000 to about 1,000:1 (e.g., from about 1:500 to about 500:1, from about 1:100 to about 100:1, from about 1:50 to about 50:1, from about 1:20 to about 20:1, from about 1:10 to about 10:1, from about 1:5 to about 5:1, from about 1:3 to about 3:1, from about 1:2 to about 2:1, about 1:1).

In certain embodiments of the use, the weight ratio of berberine or a derivative or analog of berberine, or a pharmaceutically acceptable salt thereof, to the one or more omega-3 fatty acids, or esters thereof, in the medicament is from about 10:1 to about 1:20 (e.g., from about 7:1 to about 1:20, from about 5:1 to about 1:20, from about 3:1 to about 1:20, from about 1:1 to about 1:20, from about 10:1 to about 1:15, from about 10:1 to about 1:12, from about 10:1 to about 1:10, from about 10:1 to about 1:8, from about 10:1 to about 1:5, from about 10:1 to about 1:3, from about 10:1 to about 1:1, from about 5:1 to about 1:10, from about 3:1 to about 1:10, from about 1:1 to about 1:10, from about 5:1 to about 1:5, from about 5:1 to about 1:3, from about 5:1 to about 1:1, from about 10:1 to about 5:1, from about 10:1 to about 6:1, from about 10:1 to about 7:1, from about 1:10 to about 1:20, from about 1:10 to about 1:15).

In certain embodiments of the use, the weight ratio of berberine, or a pharmaceutically acceptable salt thereof, to the one or more omega-3 fatty acids, or esters thereof, in the medicament is from about 10:1 to about 1:20 (e.g., from about 7:1 to about 1:20, from about 5:1 to about 1:20, from about 3:1 to about 1:20, from about 1:1 to about 1:20, from about 10:1 to about 1:15, from about 10:1 to about 1:12, from about 10:1 to about 1:10, from about 10:1 to about 1:8, from about 10:1 to about 1:5, from about 10:1 to about 1:3, from about 10:1 to about 1:1, from about 5:1 to about 1:10, from about 3:1 to about 1:10, from about 1:1 to about 1:10, from about 5:1 to about 1:5, from about 5:1 to about 1:3, from about 5:1 to about 1:1, from about 10:1 to about 5:1, from about 10:1 to about 6:1, from about 10:1 to about 7:1, from about 1:10 to about 1:20, from about 1:10 to about 1:15).

In certain embodiments of the use, the medicament further includes one or more agents selected from the group consisting of vitamin D, vitamin A, vitamin C, vitamin E, vitamin B, vitamin K, and calcium.

In certain embodiments of the use, the pharmaceutical composition further comprises vitamin D.

In certain embodiments of the use, the one or more omega-3 fatty acids, or esters thereof, in the medicament are provided as components of a fish oil.

In certain embodiments of the use, the fish oil is derived from tissues of oily fish, which has about 10% to about 100% of omega-3 fatty acids, or esters thereof.

In certain embodiments of the use, the medicament is in a unit dosage form comprising about 25 mg to about 100 mg of berberine or a derivative or analog of berberine, or a pharmaceutically acceptable salt thereof, and about 75 mg to about 300 mg of the one or more omega-3 fatty acids, or pharmaceutically acceptable esters thereof.

In certain embodiments of the use, the medicament is in a unit dosage form comprising about 25 mg to about 100 mg of berberine, or a pharmaceutically acceptable salt thereof, and about 75 mg to about 300 mg of the one or more omega-3 fatty acids, or pharmaceutically acceptable esters thereof.

In certain embodiments of the use, the unit dosage form is a soft gel capsule.

In certain embodiments of the use, the unit dosage form is a tablet.

In certain embodiments of the use, the unit dosage form is a liquid solution or suspension.

In certain embodiments of the use, the soft gel capsule, tablet, or liquid solution or suspension is for administration once, twice or three times daily.

In certain embodiments of the use, the medicament is used to treat a subject having ulcerative colitis.

In certain embodiments of the use, the medicament is used to treat a subject having Crohn's disease.

In certain embodiments of the use, the medicament is used to treat a subject having both ulcerative colitis and Crohn's disease.

In certain embodiments of the use, the medicament is used to treat a subject having acute inflammatory bowel disease (e.g., ulcerative colitis and/or Crohn's disease).

In certain embodiments of the use, the medicament is used to treat a subject having chronic inflammatory bowel disease (e.g., ulcerative colitis and/or Crohn's disease).

In yet another aspect, the invention generally relates to a pharmaceutical composition for treating inflammatory bowel disease, or a related disease or condition. The pharmaceutical composition includes: berberine or a derivative or analog of berberine, or a pharmaceutically acceptable salt thereof; one or more omega-3 fatty acids, or a pharmaceutically acceptable ester thereof, each being present in an amount that, when administered to a subject, is sufficient to treat inflammatory bowel disease, or a related disease or condition in a mammal, including a human.

In certain embodiments, the pharmaceutical composition includes eicosapentaenoic acid, or a pharmaceutically acceptable ester thereof.

In certain embodiments, the pharmaceutical composition includes docosahexaenoic acid, or a pharmaceutically acceptable ester thereof.

In certain embodiments of the method, the pharmaceutical composition includes only one omega-3 fatty acid, or a pharmaceutically acceptable ester thereof. In certain embodiments of the method, the pharmaceutical composition includes two or more omega-3 fatty acids, or pharmaceutically acceptable esters thereof.

In certain embodiments, the pharmaceutical composition includes eicosapentaenoic acid, or an ester thereof, and docosahexaenoic acid, or an ester thereof.

In certain embodiments, the pharmaceutical composition includes an ester (e.g., ethyl ester) of eicosapentaenoic acid and docosahexaenoic acid.

In certain embodiments, the pharmaceutical composition includes eicosapentaenoic acid and an ester (e.g., ethyl ester) of docosahexaenoic acid.

In certain embodiments, the pharmaceutical composition includes eicosapentaenoic acid and docosahexaenoic acid.

In certain embodiments, the pharmaceutical composition includes an ester (e.g., ethyl ester) of eicosapentaenoic acid and an ester (e.g., ethyl ester) of docosahexaenoic acid.

In certain embodiments of the pharmaceutical composition, the weight ratio of eicosapentaenoic acid, or an ester thereof, and docosahexaenoic acid, or an ester thereof, is from about 1:1,000 to about 1,000:1 (e.g., from about 1:500 to about 500:1, from about 1:100 to about 100:1, from about 1:50 to about 50:1, from about 1:20 to about 20:1, from about 1:10 to about 10:1, from about 1:5 to about 5:1, from about 1:3 to about 3:1, from about 1:2 to about 2:1, about 1:1).

In certain embodiments of the pharmaceutical composition, the weight ratio of berberine or a derivative or analog of berberine, or a pharmaceutically acceptable salt thereof, to the one or more omega-3 fatty acids, or esters thereof, is from about 10:1 to about 1:20 (e.g., from about 7:1 to about 1:20, from about 5:1 to about 1:20, from about 3:1 to about 1:20, from about 1:1 to about 1:20, from about 10:1 to about 1:15, from about 10:1 to about 1:12, from about 10:1 to about 1:10, from about 10:1 to about 1:8, from about 10:1 to about 1:5, from about 10:1 to about 1:3, from about 10:1 to about 1:1, from about 5:1 to about 1:10, from about 3:1 to about 1:10, from about 1:1 to about 1:10, from about 5:1 to about 1:5, from about 5:1 to about 1:3, from about 5:1 to about 1:1, from about 10:1 to about 5:1, from about 10:1 to about 6:1, from about 10:1 to about 7:1, from about 1:10 to about 1:20, from about 1:10 to about 1:15).

In certain embodiments of the pharmaceutical composition, the weight ratio of berberine, or a pharmaceutically acceptable salt thereof, to the one or more omega-3 fatty acids, or esters thereof, in the medicament is from about 10:1 to about 1:20 (e.g., from about 7:1 to about 1:20, from about 5:1 to about 1:20, from about 3:1 to about 1:20, from about 1:1 to about 1:20, from about 10:1 to about 1:15, from about 10:1 to about 1:12, from about 10:1 to about 1:10, from about 10:1 to about 1:8, from about 10:1 to about 1:5, from about 10:1 to about 1:3, from about 10:1 to about 1:1, from about 5:1 to about 1:10, from about 3:1 to about 1:10, from about 1:1 to about 1:10, from about 5:1 to about 1:5, from about 5:1 to about 1:3, from about 5:1 to about 1:1, from about 10:1 to about 5:1, from about 10:1 to about 6:1, from about 10:1 to about 7:1, from about 1:10 to about 1:20, from about 1:10 to about 1:15).

In certain embodiments, the pharmaceutical composition further includes one or more agents selected from the group consisting of vitamin D, vitamin A, vitamin C, vitamin E, vitamin B, vitamin K, and calcium.

In certain embodiments, the pharmaceutical composition further comprises vitamin D.

In certain embodiments of the pharmaceutical composition, the one or more omega-3 fatty acids, or esters thereof, are provided as components of a fish oil.

In certain embodiments of the pharmaceutical composition, the fish oil is derived from tissues of oily fish, which has about 10% to about 100% of omega-3 fatty acids, or esters thereof.

Any suitable salt of berberine or a derivative or analog of berberine may be employed. In certain embodiments of the method, the pharmaceutically acceptable salt of berberine or a derivative or analog of berberine is a chloride salt. In certain embodiments of the method, the pharmaceutically acceptable salt of berberine or a derivative or analog of berberine is a sulfate salt.

Any suitable esters of omega-3 fatty acids may be employed. As used herein, the term "pharmaceutically acceptable ester," refers to esters that hydrolyze in vivo and include those that break down readily in the human body to leave the parent compound or a salt thereof. Examples of particular esters include esters formed by an acid with a substituted or unsubstituted aliphatic alcohol (R—OH, wherein R is an alkyl group), for example, $C_1$-$C_6$ alkyl esters of eicosapentaenoic acid and of docosahexaenoic acid. Examples of $C_1$-$C_6$ alkyl esters include ethyl esters, propyl esters and butyl esters.

In certain embodiments, the pharmaceutical composition is a unit dosage form having about 10 mg to about 100 mg of berberine or a derivative or analog of berberine, or a pharmaceutically acceptable salt thereof, and about 30 mg to about 300 mg of the one or more omega-3 fatty acids, or pharmaceutically acceptable esters thereof.

In certain embodiments, the pharmaceutical composition is a unit dosage form having about 10 mg to about 100 mg of berberine, or a pharmaceutically acceptable salt thereof, and about 30 mg to about 300 mg of the one or more omega-3 fatty acids, or pharmaceutically acceptable esters thereof.

In certain embodiments of the pharmaceutical composition, the pharmaceutical composition is in the form of a soft gel capsule.

In certain embodiments of the pharmaceutical composition, the pharmaceutical composition is in the form of a tablet.

In certain embodiments of the pharmaceutical composition, the pharmaceutical composition is in the form of liquid solution or suspension.

In certain embodiments, the pharmaceutical composition is for treating ulcerative colitis.

In certain embodiments, the pharmaceutical composition is for treating Crohn's disease.

In certain embodiments, the pharmaceutical composition is for treating both ulcerative colitis and Crohn's disease.

In certain embodiments, the pharmaceutical composition is for treating acute (e.g., ulcerative colitis and/or Crohn's disease).

In certain embodiments, the pharmaceutical composition is for treating chronic (e.g., ulcerative colitis and/or Crohn's disease).

In yet another aspect, the invention generally relates to a unit dosage form comprised of a pharmaceutical composition disclosed herein.

In certain embodiments, the unit dosage form includes: from about 9 mg to about 300 mg (e.g., about 9 mg to about 250 mg, about 9 mg to about 200 mg, about 9 mg to about 150 mg, about 9 mg to about 100 mg, about 9 mg to about 75 mg, about 9 mg to about 50 mg, about 9 mg to about 25 mg, about 12.5 mg to about 300 mg, about 25 mg to about 300 mg, about 50 mg to about 300 mg, about 100 mg to about 300 mg, about 150 mg to about 300 mg, about 100 mg to about 300 mg) of berberine or a derivative or analog of berberine, or a pharmaceutically acceptable salt thereof, and from about 3 mg to about 2,400 mg (e.g., about 3 mg to about 1,800 mg, about 3 mg to about 1,200 mg, about 3 mg to about 900 mg, about 3 mg to about 600 mg, about 3 mg to about 500 mg, about 3 mg to about 250 mg, about 3 mg to about 100 mg, about 3 mg to about 75 mg, about 3 mg to about 50 mg, about 3 mg to about 25 mg, about 3 mg to about 12.5 mg, about 6 mg to about 2,400 mg, about 9 mg to about 2,400 mg, about 12.5 mg to about 2,400 mg, about 25 mg to about 2,400 mg, about 50 mg to about 2,400 mg, about 100 mg to about 2,400 mg, about 250 mg to about 2,400 mg, about 500 mg to about 2,400 mg, about 1,000 mg to about 2,400 mg, about 1,500 mg to about 2,400 mg) of one or more omega-3 fatty acids, or esters thereof.

In certain embodiments, the unit dosage form includes: from about 9 mg to about 300 mg (e.g., about 9 mg to about 250 mg, about 9 mg to about 200 mg, about 9 mg to about 150 mg, about 9 mg to about 100 mg, about 9 mg to about 75 mg, about 9 mg to about 50 mg, about 9 mg to about 25 mg, about 12.5 mg to about 300 mg, about 25 mg to about 300 mg, about 50 mg to about 300 mg, about 100 mg to about 300 mg, about 150 mg to about 300 mg, about 100 mg to about 300 mg) of berberine, or a pharmaceutically acceptable salt thereof, and from about 3 mg to about 2,400 mg (e.g., about 3 mg to about 1,800 mg, about 3 mg to about 1,200 mg, about 3 mg to about 900 mg, about 3 mg to about 600 mg, about 3 mg to about 500 mg, about 3 mg to about 250 mg, about 3 mg to about 100 mg, about 3 mg to about 75 mg, about 3 mg to about 50 mg, about 3 mg to about 25 mg, about 3 mg to about 12.5 mg, about 6 mg to about 2,400 mg, about 9 mg to about 2,400 mg, about 12.5 mg to about 2,400 mg, about 25 mg to about 2,400 mg, about 50 mg to about 2,400 mg, about 100 mg to about 2,400 mg, about 250 mg to about 2,400 mg, about 500 mg to about 2,400 mg, about 1,000 mg to about 2,400 mg, about 1,500 mg to about 2,400 mg) of one or more omega-3 fatty acids, or esters thereof.

In certain embodiments, the unit dosage form includes: from about 25 mg to about 300 mg of berberine, or a pharmaceutically acceptable salt thereof, and from about 75 mg to about 900 mg of one or more omega-3 fatty acids, or esters thereof.

In certain embodiments, the unit dosage form includes: from about 25 mg to about 300 mg of berberine or a derivative or analog of berberine, or a pharmaceutically acceptable salt thereof, and from about 75 mg to about 900 mg of eicosapentaenoic acid, or an ester thereof.

In certain embodiments, the unit dosage form includes: from about 25 mg to about 300 mg of berberine, or a pharmaceutically acceptable salt thereof, and from about 75 mg to about 900 mg of eicosapentaenoic acid, or an ester thereof.

In certain embodiments, the unit dosage form includes: from about 25 mg to about 300 mg of berberine or a derivative or analog of berberine, or a pharmaceutically acceptable salt thereof, and from about 75 mg to about 900 mg of docosahexaenoic acid, or an ester thereof.

In certain embodiments, the unit dosage form includes: from about 25 mg to about 300 mg of berberine, or a pharmaceutically acceptable salt thereof, and from about 75 mg to about 900 mg of docosahexaenoic acid, or an ester thereof.

In certain embodiments, the unit dosage form includes: from about 10 mg to about 300 mg of berberine or a derivative or analog of berberine, or a pharmaceutically acceptable salt thereof, and from about 15 mg to about 531 mg of eicosapentaenoic acid, or an ester thereof, and from about 14 mg to about 369 mg of docosahexaenoic acid, or an ester thereof.

In certain embodiments, the unit dosage form includes: from about 10 mg to about 300 mg of berberine, or a pharmaceutically acceptable salt thereof, and from about 15 mg to about 531 mg of eicosapentaenoic acid, or an ester thereof, and from about 14 mg to about 369 mg of docosahexaenoic acid, or an ester thereof.

TABLE 2

Exemplary Dosages

| Berberine (mg) | Fish oil (mg) | Vitamin D3 (IU) |
| --- | --- | --- |
| 10 | 10-200 | 0-1000 |
| 25 | 10-500 | 0-1000 |
| 50 | 20-900 | 0-1000 |
| 75 | 25-900 | 0-1000 |
| 100 | 50-900 | 0-1000 |
| 150 | 50-900 | 0-1000 |
| 200 | 100-900 | 0-1000 |
| 250 | 100-900 | 0-1000 |
| 300 | 100-900 | 0-1000 |

In yet another aspect, the invention generally relates to a kit that includes: (i) berberine or a derivative or analog of berberine, or a pharmaceutically acceptable salt thereof; (ii) one or more omega-3 fatty acids, or esters thereof; iii) optionally one or more agent(s) selected from the group consisting of vitamin D, vitamin A, vitamin C, vitamin E, vitamin B, vitamin K, and calcium; and instructions for administering agents (i), (ii) and (iii) to a patient having inflammatory bowel disease or a related disease or condition. Each of the compound(s) of (i) and (ii) can be either a purified or synthetic active pharmaceutical ingredient; or as an active ingredient from natural extracts, for examples: goldenseal root extract (berberine), fish oil (omega-3 fatty acid).

In yet another aspect, the invention generally relates to a kit that includes: (i) berberine or a derivative or analog of berberine, or a pharmaceutically acceptable salt thereof; (ii) one or more omega-3 fatty acids, or esters thereof; (iii) vitamin D; and instructions for administering agents (i), (ii) and (iii) to a patient having inflammatory bowel disease or a related disease or condition.

In certain embodiments, the pharmaceutical composition includes a pharmaceutically acceptable excipient, carrier, or diluent.

The following examples are meant to be illustrative of the practice of the invention, and not limiting in any way.

EXAMPLES

Example 1

Pharmacological Effects in DSS-induced Acute IBD Mouse Model

After a 1-week acclimation, C57BL/6J male mice with the body weight of ~20 g were randomly divided into 6 groups of 10 mice each. Five groups were assigned to establish an acute IBD mouse model by adding 3% (W/V) dextran sulfate sodium (DSS) in drinking water for 9 consecutive days, and one group was designated as normal control without adding DSS in drinking water. The 5 model groups were randomly assigned as the model control group (vehicle), positive control group (50 mg/kg cyclosporin A), BBR group (50 mg/kg berberine chloride), Fish Oil group (150 mg/kg fish oil containing 47.8% (w/w) EPA-ethyl ester and 39.0% (w/w) DHA-ethyl ester) or Test Composition group (50 mg/kg berberine chloride+150 mg/kg fish oil containing 47.8% (w/w) EPA-ethyl ester and 39.0% (w/w) DHA-ethyl ester), as indicated in Table 3.

TABLE 3

Study Design

| Group | Model Establishment | Treatment |
| --- | --- | --- |
| 1 Normal Control | Drinking water without DSS | Soybean oil |
| 2 Model Control | Drinking water with 3.5% DSS for 9 days | Soybean oil |
| 3 Positive Control | Drinking water with 3.5% DSS for 9 days | 50 mg/kg cyclosporin A |
| 4 BBR | Drinking water with 3.5% DSS for 9 days | 50 mg/kg berberine |
| 5 Fish Oil | Drinking water with 3.5% DSS for 9 days | 150 mg/kg fish oil |
| 6 Test Composition | Drinking water with 3.5% DSS for 9 days | 50 mg/kg berberine + 150 mg/kg fish oil |

Treatment was initiated on the first day of DSS administration. Mice were administrated test articles via oral gavage once daily for 9 consecutive days. During the study period, the body weight was monitored and recorded. Feces status of diarrhea or bleeding, which indicated intestinal damage, was observed and scored according to severity. Feces were also collected for neutrophil gelatinase-associated lipocalin (NGAL) concentration determination on day 7. The study was terminated on day 10, and colons were harvested for length determination. Comparing to the model control group, all the treatment groups demonstrated beneficial effects as evidenced by smaller body weight loss, diarrhea and bleeding attenuation, lower NGAL concentration and reduced colon length shortening. FIG. 1 shows the body weight changes of each group at the end of the study. FIG. 2 and FIG. 3 show the diarrhea and bleeding scores of each group on day 9. FIG. 4 shows the NGAL concentration on day 7. FIG. 5 shows the colon length after a 9-day treatment period.

It is of note that comparing to berberine or fish oil treatment alone, the group treated with the test composition exhibited the most profound therapeutic effects with the least body weight loss, the lowest diarrhea and bleeding score, and the longest colon length. These results support that synergistic effect of the test composition in treating IBD.

Example 2

Pharmacological Effects in DSS-Induced Acute IBD Mouse Model

After a 1-week acclimation, C57BL/6J male mice with the body weight of ~20 g were randomly divided into 5 groups of 10 mice each. Four groups were assigned to establish an acute IBD mouse model by adding 3% (W/V) dextran sulfate sodium (DSS) in drinking water for 7 consecutive days, and one group was designated as normal control without adding DSS in drinking water. The 4 model groups were randomly assigned as the model control group (vehicle), positive control group (50 mg/kg cyclosporin A), low dose test composition (Test Comp-L) or high dose test composition (Test Comp-H) on the first day of DSS induction and lasted for 7 days. The body weight and colon length were recorded on the day of study termination. Test Comp-L contains: 50 mg/kg berberine chloride, 136 mg/kg fish oil comprises 32.8 mg/kg EPA-ethyl ester and 23.5 mg/kg DHA-ethyl ester, and 65 IU/kg Vitamin D3; Test Comp-H contains: 150 mg/kg berberine chloride, 408 mg/kg fish oil comprises 98.4 mg/kg EPA-ethyl ester and 70.5 mg/kg DHA-ethyl ester, and 195 IU/kg Vitamin D3, as described in Table 4.

TABLE 4

Study Design

| Group | Model Establishment | Treatment |
|---|---|---|
| 1 Normal Control | Drinking water without DSS | Soybean oil |
| 2 Model Control | Drinking water with 3.5% DSS for 7 days | Soybean oil |
| 3 Positive Control | Drinking water with 3.5% DSS for 7 days | 50 mg/kg cyclosporin A |
| 4 Test-Comp L | Drinking water with 3.5% DSS for 7 days | 50 mg/kg berberine; 136 mg/kg fish oil; 65 IU/kg Vitamin D3 |
| 5 Test-Comp H | Drinking water with 3.5% DSS for 7 days | 150 mg/kg berberine; 408 mg/kg fish oil; 195 IU/kg Vitamin D3 |

Treatment was initiated on the first day of DSS administration. Mice were administrated test articles via oral gavage once daily for 7 consecutive days. During the study period, the body weight was monitored and recorded. The body weight and colon length were recorded on the day of study termination.

Compared with the model control group, less body weight loss and longer colon length were observed in both of the test composition treated groups (FIG. 6 and FIG. 7). The beneficial effect of the test composition was dose dependent in that Test-Comp H demonstrated stronger effects than that of Test-Comp L.

Example 3

Pharmacokinetic Properties of the Combination of Berberine and Fish Oil in Rats

This example describes the in vivo study in rats on pharmacokinetic (PK) properties of the combination of berberine and fish oil disclosed in the present invention.

In the single-dose pharmacokinetic study in rats, after 7-day acclimation, healthy male Sprague-Dawley (SD) rats with the body weight of 210-250 g were randomized into six groups as follows (3 rats per group). Fish oil used in this study containing 47.8% (w/w) EPA-ethyl ester and 39.0% (w/w) DHA-ethyl ester.

TABLE 5

Group Design

| Group | Test Articles |
|---|---|
| 1 | Vehicle (0.5% gum tragacanth) |
| 2 | BBR 100 mg/kg |
| 3 | BBR 100 mg/kg + Fish oil 30 mg/kg |
| 4 | BBR 100 mg/kg + Fish oil 100 mg/kg |
| 5 | BBR 100 mg/kg + Fish oil 300 mg/kg |
| 6 | Fish oil 300 mg/kg |

TABLE 5-continued

Group Design

| Group | Test Articles |
|---|---|
| 7 | BBR 100 mg/kg + Fish oil 800 mg/kg |
| 8 | Fish oil 800 mg/kg |

The rats in each group were orally treated with the suspensions of the corresponding testing articles indicated above in 0.5% gum tragacanth respectively. Blood samples of the test animals were collected pre-dose and at the time points of 15 min, 30 min, 1 h, 1.5 h, 2 h, 4 h, 8 h, and 24 h post-dose. The collected blood samples (approximately 400 µL) were placed into tubes containing heparin sodium and centrifuged at 8000 rpm for 6 minutes at 4° C. to separate plasma. The obtained plasma from each sample was stored at −80° C. until being analyzed.

Plasma concentrations of BBR and EPA were determined, and PK parameters were calculated. The resulted $C_{max}$ and $AUC_{0-t}$ parameters of EPA (Table 6 and Table 7) and BBR (Table 6) demonstrated that the combination of berberine and fish oil improved the pharmacokinetic properties of each other.

TABLE 6

Selected PK Parameters of EPA in SD Rats Following Single Oral Administration

| | Group | $C_{max}$ (ng/mL) | $C_{max}$ (ng/mL) (Normalized by subtracting the endogenous EPA) |
|---|---|---|---|
| 1 | Vehicle | 1271.59 ± 150.69 | 0.00 |
| 5 | BBR 100 mg/kg + Fish oil 300 mg/kg | 3717.06 ± 499.09 | 2445.47 |
| 6 | Fish oil 300 mg/kg | 2384.25 ± 611.70 | 1112.66 |
| 7 | BBR 100 mg/kg + Fish oil 800 mg/kg | 3967.47 ± 664.62 | 2695.88 |
| 8 | Fish oil 800 mg/kg | 4757.22 ± 768.77 | 3485.63 |

TABLE 7

Selected PK Parameters of EPA in SD Rats Following Single Oral Administration

| | Group | $AUC_{0-t}$ (ng · h/mL) | $AUC_{0-t}$ (ng · h/mL) (Normalized by subtracting the endogenous EPA) |
|---|---|---|---|
| 1 | Vehicle | 10107.76 ± 2591.07 | 0.00 |
| 5 | BBR 100 mg/kg + Fish oil 300 mg/kg | 26970.51 ± 3632.38 | 16862.75 |

TABLE 7-continued

Selected PK Parameters of EPA in SD Rats Following Single Oral Administration

| | Group | $AUC_{0-t}$ (ng · h/mL) | $AUC_{0-t}$ (ng · h/mL) (Normalized by subtracting the endogenous EPA) |
|---|---|---|---|
| 6 | Fish oil 300 mg/kg | 16254.39 ± 3411.10 | 6146.63 |
| 7 | BBR 100 mg/kg + Fish oil 800 mg/kg | 33218.55 ± 7968.83 | 23110.79 |
| 8 | Fish oil 800 mg/kg | 25000.64 ± 3262.75 | 14892.88 |

TABLE 8

Selected PK Parameters of BBR in SD Rats Following Single Oral Administration

| | Group | $C_{max}$ (ng/mL) | Ratio of $C_{max}$ compared to BBR group | $AUC_{0-t}$ (ng · h/mL) | Ratio of $AUC_{0-t}$ compared to BBR group |
|---|---|---|---|---|---|
| 2 | BBR 100 mg/kg | 4.23 ± 5.46 | 1.00 | 45.82 ± 60.13 | 1.00 |
| 3 | BBR 100 mg/kg + Fish oil 30 mg/kg | 4.24 ± 3.31 | 1.00 | 49.14 ± 39.09 | 1.07 |
| 4 | BBR 100 mg/kg + Fish oil 100 mg/kg | 6.17 ± 3.01 | 1.46 | 58.83 ± 22.06 | 1.28 |
| 5 | BBR 100 mg/kg + Fish oil 300 mg/kg | 6.62 ± 1.47 | 1.57 | 64.59 ± 11.38 | 1.41 |
| 7 | BBR 100 mg/kg + Fish oil 800 mg/kg | 15.58 ± 10.39 | 3.68 | 100.29 ± 27.69 | 2.19 |

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

Incorporation by Reference

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. A method for treating or reducing inflammatory bowel disease, comprising administering to a subject in need thereof a therapeutically effective amount of a pharmaceutical composition consisting of:
    (a) berberine, or a chloride, sulfate or citrate salt thereof,
    (b1) ethyl ester of eicosapentaenoic acid,
    (b2) ethyl ester of docosahexaenoic acid, and
    (c) a pharmaceutically acceptable excipient, carrier or diluent,
wherein
    the weight ratio of (a) to (b1) and (b2) is about 1:3,
    the weight ratio of ethyl ester of eicosapentaenoic acid to ethyl ester of docosahexaenoic acid is from about 1:2 to about 2:1, and
    the pharmaceutical composition does not contain any active agent that elicits a biological response, other than the said (a), (b1) and (b2).

2. The method of claim 1, wherein the pharmaceutical composition is administered in a unit dosage form that is a soft gel capsule.

3. The method of claim 2, wherein the soft gel capsule is administered from once, twice or three times daily.

4. The method of claim 2, wherein the inflammatory bowel disease is acute ulcerative colitis.

5. The method of claim 2, wherein the inflammatory bowel disease is acute Crohn's disease.

* * * * *